US010849616B2

(12) United States Patent
Dooney, Jr. et al.

(10) Patent No.: US 10,849,616 B2
(45) Date of Patent: Dec. 1, 2020

(54) REINFORCED GRAFT CONSTRUCTS AND METHODS OF TISSUE REPAIRS

(71) Applicant: ARTHREX, INC., Naples, FL (US)

(72) Inventors: Thomas Dooney, Jr., Naples, FL (US); Orr Limpisvasti, Anaheim, CA (US); Thay Q. Lee, La Canada Flintridge, CA (US)

(73) Assignee: ARTHREX, INC., Naples, FL (US)

( * ) Notice: Subject to any disclaimer, the term of this patent is extended or adjusted under 35 U.S.C. 154(b) by 143 days.

(21) Appl. No.: 16/141,417

(22) Filed: Sep. 25, 2018

(65) Prior Publication Data

US 2020/0093481 A1    Mar. 26, 2020

(51) Int. Cl.
| | |
|---|---|
| *A61B 17/06* | (2006.01) |
| *A61B 17/04* | (2006.01) |
| *A61L 17/00* | (2006.01) |
| A61L 27/58 | (2006.01) |
| A61B 17/02 | (2006.01) |
| A61L 31/04 | (2006.01) |

(52) U.S. Cl.
CPC .... *A61B 17/06166* (2013.01); *A61B 17/0401* (2013.01); *A61L 17/00* (2013.01); *A61B 2017/0225* (2013.01); *A61B 2017/0464* (2013.01); *A61L 27/58* (2013.01); *A61L 31/044* (2013.01); *A61L 2430/10* (2013.01)

(58) Field of Classification Search
CPC .......... A61B 17/06166; A61B 17/0401; A61B 17/0485; A61B 17/04; A61B 17/06
See application file for complete search history.

(56) References Cited

U.S. PATENT DOCUMENTS

| | | | |
|---|---|---|---|
| 4,037,603 A | 7/1977 | Wendorff | |
| 4,455,690 A | 6/1984 | Homsy | |
| 5,061,283 A | 10/1991 | Silvestrini | |
| 6,106,556 A | 8/2000 | Demopulos et al. | |
| 6,712,830 B2 | 3/2004 | Esplin | |
| 7,329,271 B2 | 2/2008 | Koyfman et al. | |
| 7,410,460 B2 | 8/2008 | Benderev | |
| 7,883,518 B1 * | 2/2011 | Davies ............... | A61B 17/0469 606/148 |
| 7,892,256 B2 | 2/2011 | Grafton et al. | |
| 8,298,284 B2 | 10/2012 | Cassani | |
| 8,439,976 B2 | 5/2013 | Albertorio et al. | |
| 8,545,535 B2 | 10/2013 | Hirotsuka et al. | |
| 8,591,544 B2 | 11/2013 | Jolly et al. | |

(Continued)

*Primary Examiner* — Vi X Nguyen
(74) *Attorney, Agent, or Firm* — Potomac Law Group PLLC (57) ABSTRACT

Surgical constructs, assemblies and methods for tissue reinforcement with a reinforcement (reinforcing) material such as suture, tape, weave, ribbon or mesh, among many others. The reinforced construct includes a reinforced section that prevents a suture from pulling apart. The reinforced section is be a piece of material (a reinforcement or reinforcing material) such as reinforced stitched suture tape attached to a flexible strand. A needle attached to the flexible strand terminating with the reinforced section passes through a proximal end of the reinforced section to form an adjustable "starter loop." The starter loop is slid and positioned over tissue (for example, graft, tendon, ligament, etc.) and the suture is pulled apart to tighten the loop around the tissue.

13 Claims, 6 Drawing Sheets

(56) References Cited

U.S. PATENT DOCUMENTS

| | | |
|---|---|---|
| 8,936,621 B2* | 1/2015 | Denham ............ A61B 17/0401 |
| | | 606/232 |
| 9,168,124 B2 | 10/2015 | Guerra et al. |
| 9,486,211 B2* | 11/2016 | Stone ................. A61B 17/0482 |
| 9,622,742 B2 | 4/2017 | Spenciner |
| 9,649,189 B2 | 5/2017 | Konicek |
| 9,907,593 B2 | 3/2018 | McDonnell |
| 9,993,332 B2 | 6/2018 | Woodruff et al. |
| 10,363,028 B2* | 7/2019 | Norton ............... A61B 17/0485 |
| 10,385,488 B1* | 8/2019 | Monllor ................... D01H 4/00 |
| 2003/0153947 A1 | 8/2003 | Koseki |
| 2009/0318962 A1 | 12/2009 | Spedden et al. |
| 2011/0251639 A1* | 10/2011 | Thomas ........... A61B 17/06166 |
| | | 606/228 |
| 2012/0296345 A1* | 11/2012 | Wack ................. A61B 17/0483 |
| | | 606/139 |
| 2013/0116799 A1 | 5/2013 | Derwin et al. |
| 2014/0277448 A1* | 9/2014 | Guerra ............... A61B 17/0401 |
| | | 623/13.14 |
| 2016/0175088 A1 | 6/2016 | Sengun |
| 2017/0181739 A1 | 6/2017 | Breslich |
| 2017/0189162 A1 | 7/2017 | Spenciner |

* cited by examiner

REINFORCED GRAFT CONSTRUCTS AND METHODS OF TISSUE REPAIRS

BACKGROUND

The disclosure relates to the field of surgery and, more specifically, to reinforced constructs and tissue repairs for reconstructive surgeries.

SUMMARY

Surgical constructs, assemblies and methods for tissue to bone repair employing a tissue construct reinforced with a reinforcement (reinforcing) material such as suture, tape, weave, ribbon or mesh, among many others, are disclosed.

The reinforced construct includes a reinforced section that prevents a suture from pulling apart. The reinforced section may be a piece of material (a reinforcement or reinforcing material) such as reinforced suture tape attached to a flexible strand. A needle attached to the flexible strand terminating with the reinforced section passes through a proximal end of the reinforced section to form an adjustable "starter loop." The starter loop is slid or positioned over tissue (for example, graft, tendon, ligament, etc.) and the suture is pulled apart to tighten the loop around the tissue. The reinforced section is positioned over a tissue surface. A plurality of stitches are conducted through both the reinforced section and the tissue to reinforce tissue.

DETAILED DESCRIPTION

The disclosure provides surgical systems, assemblies, constructs, and methods for tissue reinforcement with a reinforced graft construct, as well as methods of securing soft tissue to bone with a reinforced graft construct.

In an embodiment, a suture loop construct includes a unique reinforced tape suture that prevents the suture from pulling apart. The tape may be reinforced with additional stitching. The construct increases the overall pull strength between the suture and graft. The reinforced section of the suture can be intentionally long and trimmed to fit. As detailed below, this area is reinforced to prevent the suture from pulling apart since sutures will be passed through the actual suture. A needle attached to suture tape goes through the proximal end of the reinforced area forming an adjustable "starter loop." Suture tape extends up to the needle for the remaining suture length.

In an exemplary embodiment, a surgical construct is a reinforced tissue construct that includes a flexible strand with a first end and a second end, and a needle attached to one of the first and second ends. A starter loop and a reinforcement material are provided at the other of the first and second ends of the flexible strand. In an exemplary embodiment, at least a portion of the reinforcement material forms the starter loop. The starter loop may be adjustable, i.e., may have an adjustable length and/or perimeter. The starter loop is a continuous, uninterrupted, flexible, knotless loop. The starter loop may be formed by passing the needle attached to the flexible strand, and passing the flexible strand, through the reinforcement material, for example, at a location proximal to an end of the reinforcement material.

The reinforced tissue constructs of the present disclosure preferably include a stitched region formed by employing a suture loop/needle assembly with (1) a needle that is attached to a continuous length of flexible material (suture); (2) an adjustable starter loop formed by the flexible material; (3) a piece of reinforcement material attached to the continuous starter loop. As detailed below, the piece of reinforcement material is attached/affixed to at least a portion of the tissue (graft, ligament or tendon) to reinforce the tissue. The material may be any reinforcement (reinforcing) material such as suture, tape, ribbon, weave, or mesh that can be attached (sutured) to the tissue. The material may be reinforced by stitching. In an exemplary-only embodiment, the flexible material is a suture tape such as FiberTape® (U.S. Pat. No. 7,892,256) manufactured by Arthrex, Inc. Naples, Fla., or a collagen tape, or a combination of these materials; the reinforcement material may be a ribbon, tape or any material with a width greater than that of the flexible material (for example, a suture tape with a width greater than that of FiberTape® suture). The reinforcement material may be attached to the tissue by suturing (for example, stitching such as whipstitching) or by any other affixing/attachment techniques, to provide additional fixation when tissue is implanted.

The present disclosure also provides methods of forming reinforced tissue constructs having increased pull-out strength as well as methods of securing such reinforced tissue constructs in bone tunnels or sockets. An exemplary method of forming a reinforced tissue construct (reinforced biologic construct) according to the present disclosure comprises inter alia the steps of: (i) securing a starter loop of a suture loop/needle assembly around tissue (the suture loop/needle assembly comprising a flexible strand, a needle attached at one end of the flexible strand, and a continuous, uninterrupted, flexible, adjustable, knotless loop and a reinforcement material attached at the other end of the flexible strand); positioning the reinforcement material over a tissue surface; and suturing/stitching at least a portion of the tissue and of the reinforcement material. The step of securing the starter loop may include sliding the starter loop over the tissue and tightening the starter loop around the tissue (by pulling on the flexible strand).

Figure 1:
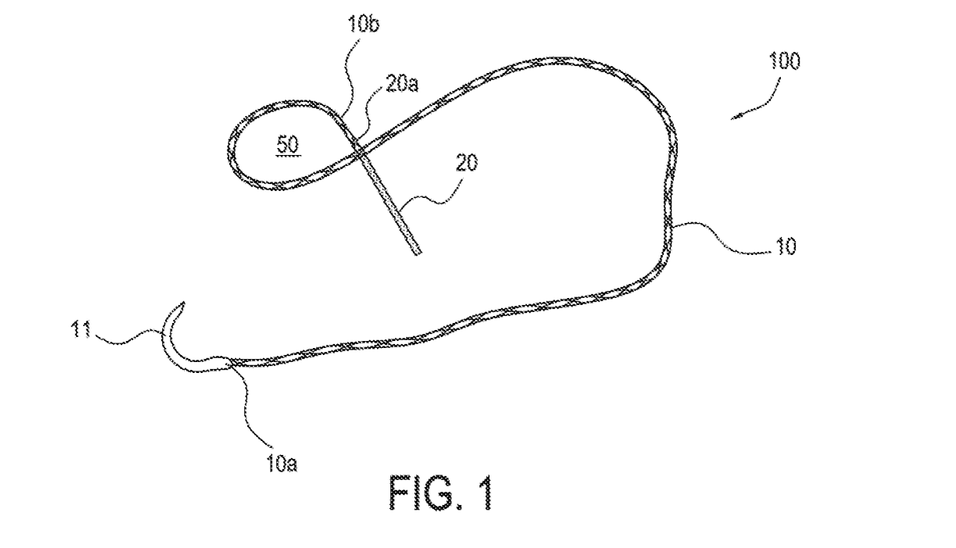
FIG. 1 illustrates a surgical construct according to an exemplary embodiment.
Figure 2:
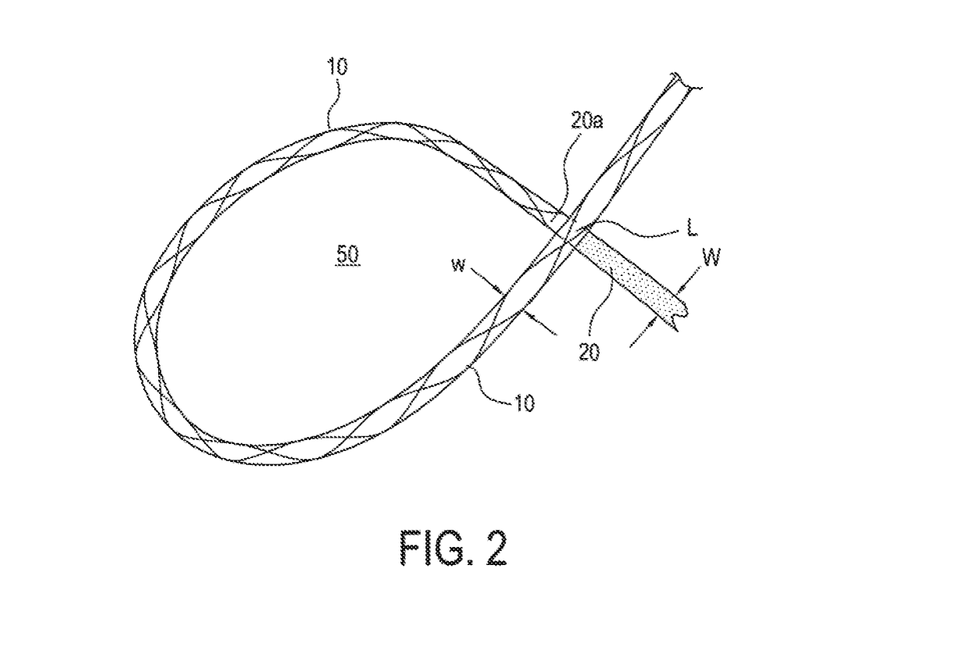
FIG. 2 illustrates an enlarged view of the starter loop of the construct of FIG. 1.

Referring now to the drawings, where like elements are designated by like reference numerals, FIGS. 1 and 2 illustrate surgical construct 100 (suture loop/needle assembly 100; suture loop/needle construct 100; reinforcement construct 100) of the present disclosure. FIGS. 3-13 illustrate steps of tissue repair 101 with exemplary surgical constructs. FIG. 14 illustrates various exemplary suture/stitching configurations with the constructs of the present disclosure.

FIG. 1 illustrates exemplary surgical construct 100 which is a flexible suture loop/needle assembly that includes a flexible strand or flexible material 10 provided with a first end 10a and a second end 10b. A needle 11 is attached to, or at, one of the ends 10a, 10b of the flexible strand 10 (for example, at end 10a), as shown in FIG. 1. Needle 11 may be a thin nitinol needle with a curved or straight configuration, preferably crimped or swaged on the flexible strand 10. The thin needle 11 is preferably curved to facilitate subsequent suturing/stitching of tissue, as detailed below.

Surgical construct 100 of FIG. 1 also comprises a continuous, uninterrupted, flexible, adjustable, knotless loop 50 with an attached piece of material 20 (reinforcement material 20; reinforcing material 20), both provided at the end of the flexible strand 10 opposite to that where the needle 11 attaches, i.e., at end 10b. Knotless, adjustable, closed, flexible loop 50 is a continuous, uninterrupted loop formed by passing the needle 11 through an end of the reinforcement material 20, for example, through end 20a. FIG. 2 is an enlarged view of the starter loop 50, showing flexible strand 10 passed through the reinforcement material 20 at location L which is proximal to end 20a.

In an exemplary embodiment, flexible strand 10 may be formed of suture or suture tape, or combination of these materials, which will also form the continuous loop 50 of suture 10. The flexible strand 10 may be suture tape such as FiberTape® or collagen tape, or combinations thereof.

Reinforcement material 20 is attached to the continuous suture loop 50 and to the flexible strand 10. Material 20 may be any reinforcement/reinforcing material that can be attached (sutured) to the tissue (tendon/graft/ligament). In exemplary only embodiments, the reinforcement material may be suture, tape, weave, ribbon, or mesh, or any combinations of these materials, as long as the width "W" of the reinforcement material is greater than the width "w" or diameter of the flexible strand. The reinforcement material 20 may be provided with various medicinal or therapeutic agents, for example, antiseptics, antibiotics, drugs, pharmaceutical agents, hormones and growth materials (for example, autogenous growth factors such as platelet-rich plasma (PRP), autologous factors, autologous-conditioned plasma (ACP)), among many others). The reinforcement material 20 may be stitched throughout its length, for additional reinforcement.

The reinforcement material 20 may have any shape and geometry that provides reinforcement to the tissue to be sutured. For example, and according to an exemplary-only embodiment, the reinforcement material may have a rectangular configuration (as shown in FIGS. 1 and 2) with a length of about 22.5 mm, or any configuration as long as it provides a surface area on which suturing/stitching may be conducted. The reinforcement material 20 may be provided in any length/width and then cut depending upon the configuration and geometry of the tissue (graft) to be reinforced. The reinforcement material 20 may be FiberTape® that could be provided longer and/or wider. The reinforcement material 20 may be attached to the flexible strand 10 by any method known in the art, for example, by gluing, braiding, swedging or knotting, among many others. Preferably, the length of the reinforcement material 20 approximates the length of the tendon/ligament/graft that will be stitched.

Figure 3:
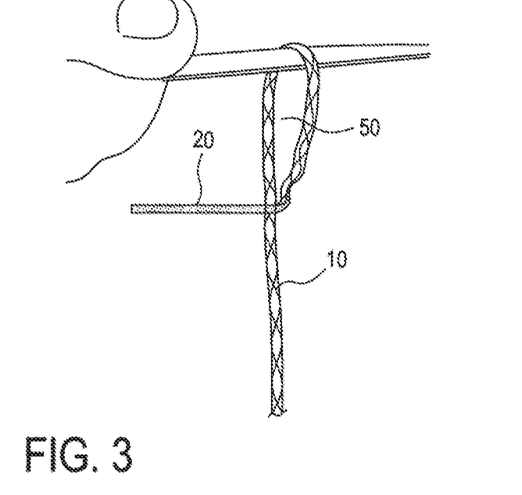
FIGS. 3-13 illustrate a method of attaching the construct of FIG. 1 to tissue.

FIG. 3 illustrates another view of construct 100 with starter loop 50 over a surgical instrument and reinforcement material 20 secured to it. As detailed below, starter loop 50 will be slid/positioned over tissue 80 (for example, graft or tendon 80 or any soft tissue) and then tightened/secured around the tissue. The reinforcement material 20 is positioned over a surface of graft 80, aligned with a distal aspect of the graft 80 and held in place with a clamp (for example, an Alice clamp).

An exemplary method of reinforcing tissue 80 with a construct of the present disclosure is set forth below with reference to FIGS. 3-13:

FIG. 3

Slide the starter loop 50 of construct 100 over the tendon 80.

Figure 4:
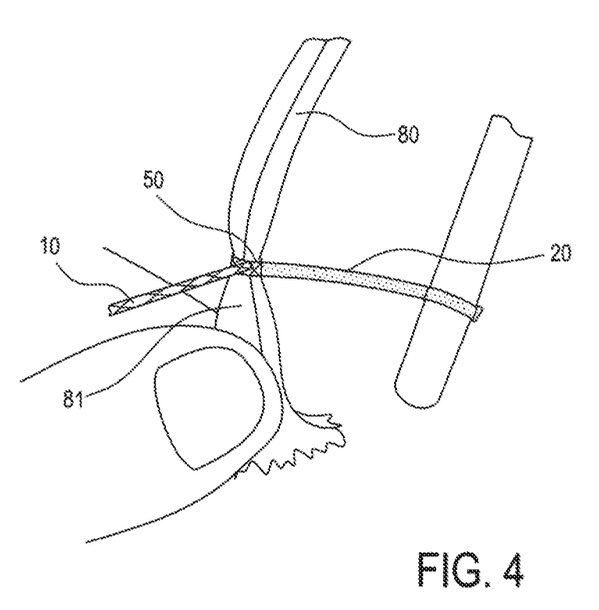

FIG. 4

Pull the suture 10 apart to tighten loop 50 around tendon 80.

Figure 5:
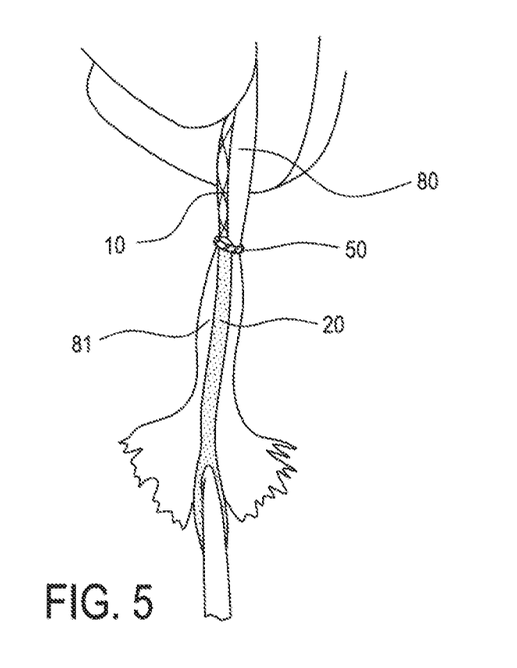

FIG. 5

The blue section represents the reinforced material 20 (reinforced suture 20), for example, a typical suture tape provided with the blue stitch (a reinforcement stitch) that keeps the suture together and prevents it from pulling apart when another suture passes through it. Reinforcement material 20 is positioned/placed over surface 81 of tendon 80.

Figure 6:
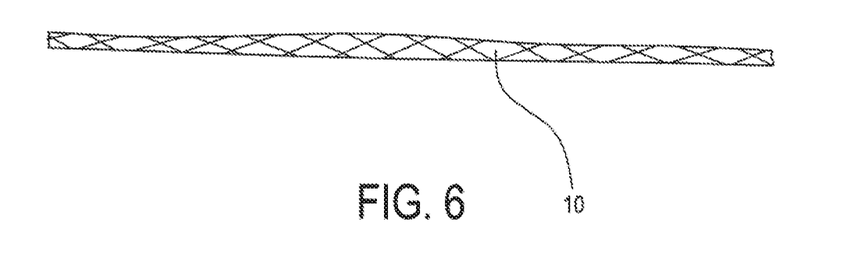

FIG. 6

The black/white suture 10 is a suture tape without reinforcement.

Figure 7:
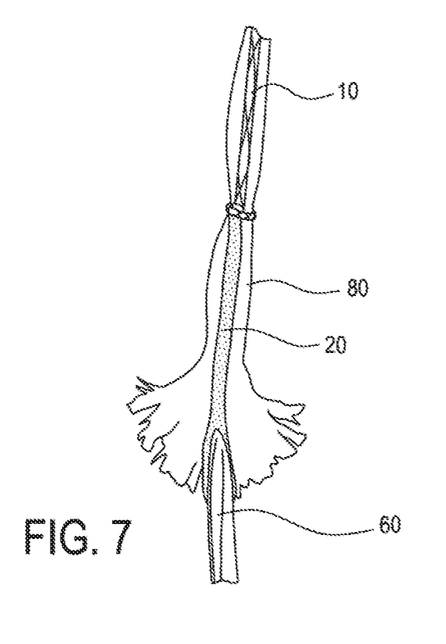

FIG. 7

Apply a hemostat 60 on distal end of tendon 80 and on reinforcement material 20 (suture tape 20). Pull the hemostat 60 and opposing suture strand 10 apart and the loop 50 will slide proximal up to the tendon 80 removing any slack in the construct.

Figure 8:
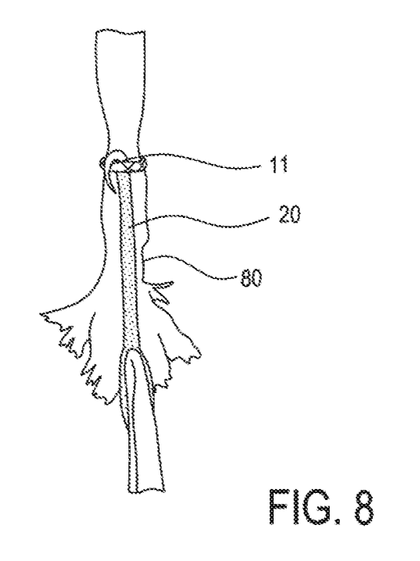

FIG. 8

Pass the needle 11 through the reinforced area 20 of the suture tape and tendon 80. Pull tight to lock into position.

Figure 9:
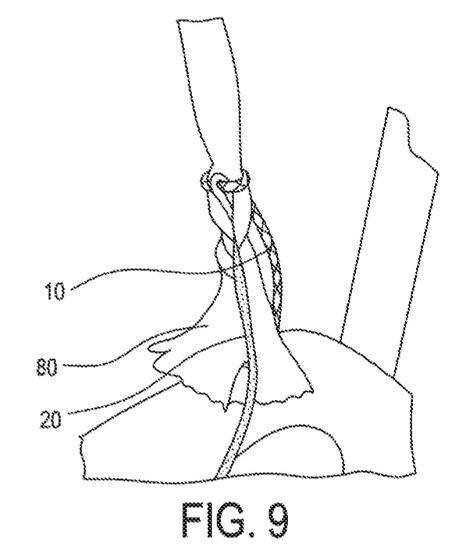

FIG. 9

Wrap suture 10 around tendon 80 and pierce both SutureTape 20 and tendon 80 proximal to the new loop 31 with needle 11. Pull tight to remove any slack.

Figure 10:
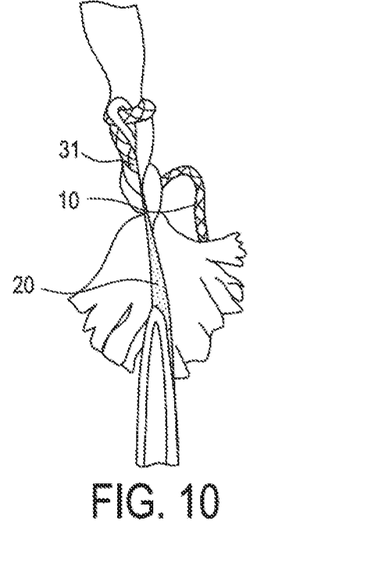
Figure 11:
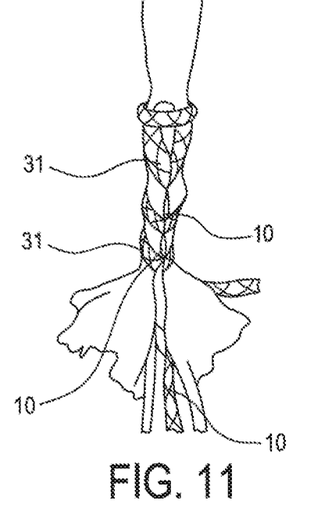
Figure 12:
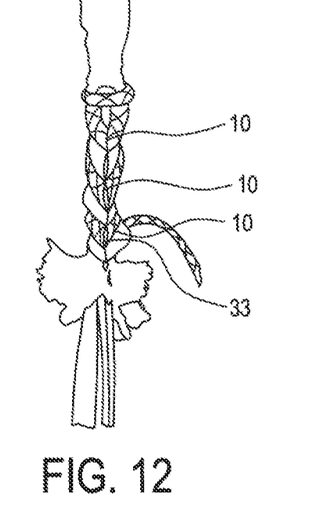

FIGS. 10-12

Repeat the previous steps to complete the stitch 33 (FIG. 12) formed of plurality of stitching loops 31.

Figure 13:
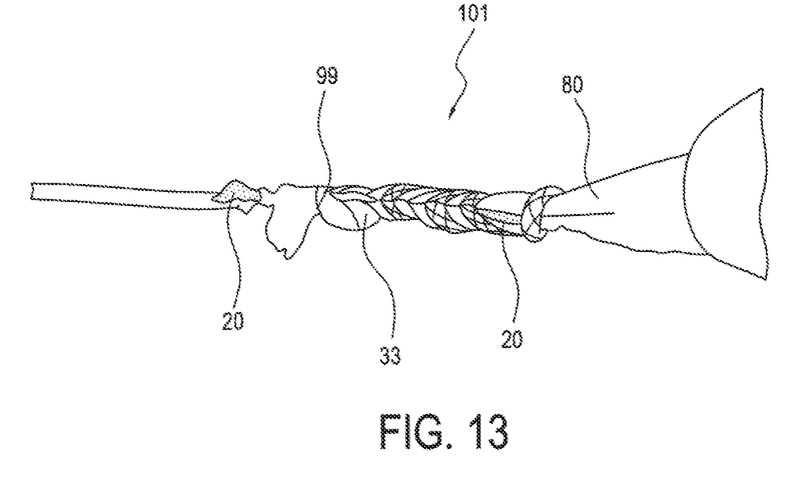
Figure 14:
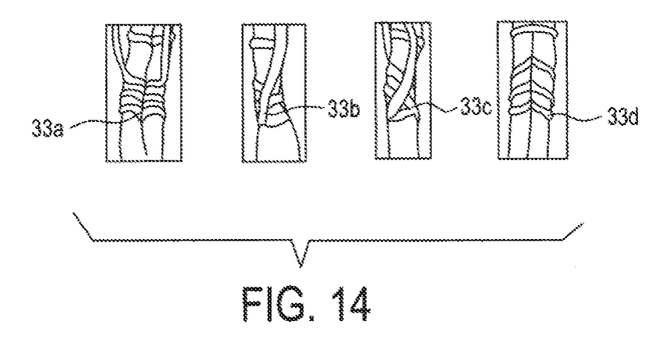
FIG. 14 illustrates various exemplary suture configurations with the construct of FIG. 1.

FIG. 13

The reinforced graft construct 99 of tissue repair 101 is formed by the suture loop 50 (SutureLoop 50) which self-reinforces itself and improves the pull strength between the suture 10 and tissue 80 when compared to existing techniques. The stitch technique of the present disclosure also compresses the tissue 80 more than other techniques, to help it fit into smaller bones.

FIG. 14 illustrates various stitching configurations 33a, 33b, 33c, 33d (suturing or stitching patterns 33a, 33b, 33c, 33d) achieved with the surgical constructs of the present disclosure.

Reinforcement material 20 (reinforcing material 20) of construct 100 is stitched to the graft/ligament/tendon 80 using a needle and suture, for example, to whipstitch through the material 20 and the graft/ligament/tendon 80, to create reinforced graft assembly 99 (reinforced graft, ligament or tendon construct 99). Once the whipstitching is completed, the reinforced graft may be pre-tensioned to 20 pounds for use in ACL repair. The type of repair for which the reinforced graft construct 99 is being used for will determine the amount of pre-tensioning, which may be up to 50 pounds.

Although the above method was described using whipstitching, any type of suturing/stitching that would attach reinforcement material 20 to graft/ligament/tendon 80 could be used. Additionally, the reinforcement material 20 attached to the graft/ligament/tendon 80 may be formed in certain cases of an absorbable suture tape that would resorb away after a length of time in the body.

During an exemplary ACL reconstruction, the reinforced graft construct 99 may be secured in at least one of the tibial and femoral sockets or tunnels. These steps may be accomplished by plugging the target tunnel with a synthetic plug, bone plug or screw to contain and secure the reinforced graft construct 99 in the tunnel or, alternatively, by employing knotless lateral fixation using, for example, two knotless fixation devices (such as interference screws or graft bolttype fixation devices). The fixation devices may be preferably formed of a translucent or transparent polymer material, preferably bioabsorbable materials such as polyglycolic or polylactic acid polymers.

In another embodiment, graft insertion and fixation may be conducted by employing a continuous loop/button construct provided with a button, preferably of titanium alloy, and a continuous loop attached to the button. The button has an oblong configuration and a width that is preferably less than about 1 mm narrower than the width of the drill hole through which the button is inserted and subsequently passed through. The button is provided with an inside eyelet that allows the passage of the continuous loop. In an exemplary embodiment, the suture loop may be a single high strength suture such as FiberWire® suture. In another exemplary embodiment, the continuous loop may be formed of a plurality of suture strands configured to separate from a single strand to a plurality of strands in a continuous loop. In yet another embodiment, the loop is an adjustable loop (forming a TightRope® ACL construct) which consists of two interconnected, adjustable flexible loops formed by splicing a suture strand in a manner disclosed in U.S. Pat. No. 8,439,976 issued on May 14, 2013 and U.S. Pat. No. 8,460,379 issued on Jun. 11, 2013, the disclosures of both of which are incorporated by reference in their entireties herein.

The wide "tape like" area 20 (reinforcement or reinforcing material 20) of construct 100 is placed over the tendon/ligament/graft 80 and permits the surgeon to include the construct 100 into the tendon/ligament stitches 33. The "tape like" material 20 may include suture, FiberWire®, tape such as FiberTape®, absorbable suture, weave, mesh, ribbon, or any other material or combination of such materials that can be provided on the ligament or tendon, along a length thereon, and whipstitched to provide additional fixation when the ligament or tendon is implanted. The reinforcement material 20 may be absorbable or non-absorbable.

Construct 100 of the present disclosure allows a straight tendon (that cannot be folded) to be connected to a suspensory fixation device such as the ACL TightRope®.

The present disclosure provides methods of reinforcing tissue. In one embodiment, a method comprises inter alia (i) securing a continuous, uninterrupted, flexible, adjustable, knotless suture loop 50 of a suture loop/needle assembly 100 around tissue 80, the suture loop/needle assembly 100 comprising a flexible strand 10; a needle 11 attached to one end 10a of the flexible strand 10; a reinforcement material 20 adjacent the continuous, uninterrupted, flexible, adjustable, knotless suture loop 50 and located at other end 10b of the flexible strand 10; (ii) placing the reinforcement material 20 over a surface 81 of the tissue 80; and (iii) stitching together the reinforcement material 20 and the tissue 80, with the needle 11 and the flexible strand 10, to form a reinforced tissue construct 99 of repair 101. The method may further include the steps of forming a plurality of stitching loops 31 of stitching area/region 33, using the needle 11 attached to the flexible strand 10, through the reinforcement material 20 and the tissue 80, to stitch through the tissue 80 and the reinforcement material 20.

The present disclosure further provides methods of ligament reconstruction employing reinforced tissue constructs. An exemplary method comprises inter alia the steps of: (i) providing a target tunnel for ligament reconstruction; (ii) providing a stitched reinforced tissue construct 99 comprising at least a reinforced stitched region 33, the reinforced stitched region 33 including a reinforcement (reinforcing) material 20 located between tissue 80 (tendon/ligament/graft) and the stitching 33, the reinforcement (reinforcing) material 20 being adjacent a flexible, adjustable, knotless, uninterrupted loop 50 tightly surrounding the tissue 80; (iii) inserting the stitched tissue construct 99 into the target tunnel; and (iv) securing the stitched tissue construct 99 in the tunnel.

Flexible strand 10 and reinforcement material 20 may consist essentially of suture or suture material, or combination of suture and other materials such as long chain synthetic polymers like polyester and nylon, or materials such as PET, silk nylon or absorbable polymers, or coating materials (such as wax, silk, or silicone products), among many others. These materials augment the strength and pliability of the construct, and improve the characteristics and properties of the suture material.

The suture 10 forming the continuous loop 50 attached to reinforcement material 20 may be formed of any flexible material. In the preferred embodiment, the sutures are formed of a high strength suture material such as FiberWire® suture, sold by Arthrex, Inc. of Naples, Fla., and described in U.S. Pat. No. 6,716,234, the disclosure of which is incorporated by reference herein. The high strength suture may be available in various lengths. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material.

Flexible strand 10 and reinforcement material 20 may be formed of flexible materials and strands such as suture (for example, round suture) or tape (for example, suture tape) or combination of suture and tape. The flexible strands may have cross-sections of various forms and geometries, including round, oval, rectangular, or flat, among others, or combination of such forms and geometries. In an exemplary embodiment only, at least one of flexible strand 10 and reinforcement material 20 may be provided as a suture which may be braided, knitted or woven.

Flexible strand 10 and reinforcement material 20 may be made of any known suture construct, such as multifilament, braided, knitted, woven suture, or including fibers of ultrahigh molecular weight polyethylene (UHMWPE) or the FiberWire® suture. Flexible strand 10 and reinforcement material 20 may be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. Flexible strand 10 and reinforcement material 20 may be also formed of a stiff material, or combination of stiff and flexible materials, depending on the intended application. Flexible strand 10 and reinforcement material 20 may be also coated and/or provided in different colors.

Surgical construct 100 or parts of it may be preferably coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture or tape, knot security, pliability, handleability or abrasion resistance, for example.

Flexible strand 10 and reinforcement material 20 may be also provided with tinted tracing strands, or otherwise contrast visually with the sheath of the construct, which remains a plain, solid color, or displays a different tracing pattern, for example. Various structural elements of surgical construct 100 may be visually coded, making identification and handling of the suture legs simpler. Easy identification of suture in situ is advantageous in surgical procedures.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A method of reinforcing tissue comprising:
sliding a continuous, uninterrupted, flexible, adjustable suture loop of a suture loop/needle assembly around tissue and tightening the continuous, uninterrupted, flexible, adjustable suture loop around the tissue, the suture loop/needle assembly comprising a flexible strand; a needle attached to one end of the flexible strand; a reinforcement material adjacent the continuous, uninterrupted, flexible, adjustable suture loop and located at other end of the flexible strand;
subsequently, placing the reinforcement material over a surface of the tissue; and
stitching together the reinforcement material and the tissue, with the needle and the flexible strand, to form a reinforced tissue construct.

2. The method of claim 1, wherein the reinforcement material is a tape, a ribbon, a weave or a mesh, or combination of tape, ribbon, weave or mesh.

3. The method of claim 1, wherein the reinforcement material is a piece of first suture tape and the flexible strand is formed of a second suture tape.

4. The method of claim 3, wherein a width of the first suture tape is greater than a width of the second suture tape.

5. The method of claim 1, wherein the reinforcement material is formed of stitched suture tape.

6. The method of claim 1, wherein the tissue is a graft, a ligament or a tendon.

7. The method of claim 1 further comprising the step of pulling on the flexible strand to tighten the loop around the tissue.

8. The method of claim 1 further comprising the step of forming a plurality of stitching loops, using the needle attached to the flexible strand, through the reinforcement material and the tissue, to stitch through the tissue and the reinforcement material.

9. The method of claim 1, wherein the reinforcement material is bioabsorbable.

10. The method of claim 1, wherein the reinforcement material is separate from the flexible strand.

11. The method of claim 1, wherein the reinforcement material is separate from, and contiguous with, the flexible strand.

12. The method of claim 1, wherein the tissue is a graft.

13. The method of claim 1, wherein the tissue is an ACL graft.

\* \* \* \* \*